United States Patent
Macey et al.

(10) Patent No.: US 6,847,838 B1
(45) Date of Patent: Jan. 25, 2005

(54) APPARATUS AND METHOD FOR HIGH DOSE RATE BRACHYTHERAPY RADIATION TREATMENT

(75) Inventors: Daniel J. Macey, Birmingham, AL (US); Stanislaw Majewski, Grafton, VA (US); Andrew G. Weisenberger, Yorktown, VA (US); Mark Frederick Smith, Yorktown, VA (US); Brian James Kross, Yorktown, VA (US)

(73) Assignee: Southeastern Universities Research Assn., Inc., Newport News, VA (US)

( * ) Notice: Subject to any disclaimer, the term of this patent is extended or adjusted under 35 U.S.C. 154(b) by 46 days.

(21) Appl. No.: 10/247,450

(22) Filed: Sep. 19, 2002

(51) Int. Cl.[7] .............................................. A61B 5/05
(52) U.S. Cl. ....................... 600/431; 600/407; 600/425; 600/426; 600/436; 424/1; 424/4; 250/302; 601/2; 601/3
(58) Field of Search ................................ 600/431, 436, 600/407, 425, 426, 1, 2, 3, 8; 601/1–5; 424/1–4; 250/302

(56) References Cited

U.S. PATENT DOCUMENTS

| | | | |
|---|---|---|---|
| 3,978,337 A | * | 8/1976 | Nickles et al. .............. 250/367 |
| 5,846,513 A | * | 12/1998 | Carroll et al. ............. 424/1.11 |
| 6,135,955 A | * | 10/2000 | Madden et al. ............. 600/436 |
| 6,420,711 B2 | * | 7/2002 | Tumer ................... 250/370.09 |
| 6,510,336 B1 | * | 1/2003 | Daghighian et al. ........ 600/427 |
| 2003/0006376 A1 | * | 1/2003 | Tumer ................... 250/370.09 |
| 2004/0015075 A1 | * | 1/2004 | Kimchy et al. ............. 600/424 |

OTHER PUBLICATIONS

Feasibility Study of insitu Imaging of Ir–192 During HDR Brachytherapy Procedure Delivered at IEEE Nuclear Science Symposium Seattle, WA Oct. 29–30, 1999.

* cited by examiner

*Primary Examiner*—Brian L. Casler
*Assistant Examiner*—William C Jung

(57) ABSTRACT

A method and apparatus for the in vivo location and tracking of a radioactive seed source during and after brachytherapy treatment. The method comprises obtaining multiple views of the seed source in a living organism using: 1) a single PSPMT detector that is exposed through a multiplicity of pinholes thereby obtaining a plurality of images from a single angle; 2) a single PSPMT detector that may obtain an image through a single pinhole or a plurality of pinholes from a plurality of angles through movement of the detector; or 3) a plurality of PSPMT detectors that obtain a plurality of views from different angles simultaneously or virtually simultaneously. The plurality of images obtained from these various techniques, through angular displacement of the various acquired images, provide the information required to generate the three dimensional images needed to define the location of the radioactive seed source within the body of the living organism.

12 Claims, 2 Drawing Sheets

APPARATUS AND METHOD FOR HIGH DOSE RATE BRACHYTHERAPY RADIATION TREATMENT

The United States of America may have certain rights to this invention under Management and Operating Contract DE-AC05-84ER 40150 from the United States Department of Energy.

FIELD OF THE INVENTION

The present invention relates to high dose rate (HDR) brachytherapy treatment systems and more particularly to an improved method and apparatus for the real time, in vivo tracking of the location of the radiation source during such treatment.

BACKGROUND OF THE INVENTION

High density radiation (HDR) brachytherapy procedures depend upon delivering fractionated therapy doses to designated target volumes by timed insertion of a small (2–4 mm long) seed radiation source of, for example, Ir-192 into body cavities or tumors. The Ir-192 source is attached to a wire and pushed/pulled through previously surgically inserted catheters. Presently, HDR procedures rely on computer controlled mechanical delivery systems to track the location of the source in the body. While such a source tracking method is generally acceptable, in some case there has been movement of the surgically inserted catheter between the time of insertion and the time of brachytherapy treatment resulting in mislocation of the seed source. In extreme cases, the seed source can become "lost" in the body. In such cases, exposure of the patient to such high radiation doses for an extended period of time during the search for the seed source and removal thereof can result in the death of the patient. Thus, a device and method for the real time, in situ tracking of seed sources would be highly desirable to assure the proper location of the seed source during treatment and location of the seed source in those rare instances where it becomes lost in a body cavity or tumor during or after treatment.

Such a method and device were described in a paper entitled, "Feasibility Study of in situ Imaging of Ir-192 Source During HDR Brachytherapy Procedure Using Small Gamma Imager Based on a Hamamatsu R3292 PSPMT" presented at the IEEE Nuclear Science Symposium at Seattle, Wash. on Oct. 29–30, 1999 and subsequently published on CD in the year 2000. This paper is incorporated herein in its entirety. The apparatus described in this paper comprised a dedicated compact gamma camera based on a 5" Hamamatsu R3292 position sensitive photomultiplier and a thin Bicron BC 400 plastic scintillator. The low efficiency plastic scintillator detector provided acceptable images of a 5.3 Ci Ir-192 source when viewed through a single pin hole collimator (hole diameters 0.5 and 1.0 mm) located 16 cm from the source. While this gamma camera provided a solution to the problem of verifying HDR brachytherapy treatments, it did not provide in vivo locational information such as the exact depth of the seed source in the body. In other terms, it provided a two dimensional location on the surface of the body, but the depth of the seed within the body was not determined, thus, providing the possibility for some error in the exact location of the seed in the body cavity or tumor, and in the case of "lost" seeds, the ability to accurately locate the seed for removal.

Thus, a method and device that are capable of providing accurate, three-dimensional locational information regarding the seed source in a body cavity or tumor would be highly desirable.

OBJECT OF THE INVENTION

It is therefore an object of the present invention to provide both a method and an apparatus for the in vivo location and tracking of HDR brachytherapy treatment seed sources during and, if necessary, subsequent to the treatment regimen.

SUMMARY OF THE INVENTION

According to the present invention there are provided a method and apparatus for the in vivo location and tracking of a radioactive seed source during and, if necessary after, brachytherapy treatment. The novel apparatus described herein comprises a compact gamma camera based on a position sensitive photo multiplier tube that either; 1) views the area of the body through a collimator including a plurality of precisely located pinholes, or 2) acquires a plurality of "images" from different positions by repositioning the compact gamma camera or the use of multiple gamma cameras to obtain a plurality of images that can be used to reconstruct the location of the seed source in three dimensional space.

DETAILED DESCRIPTION

Figure 1:
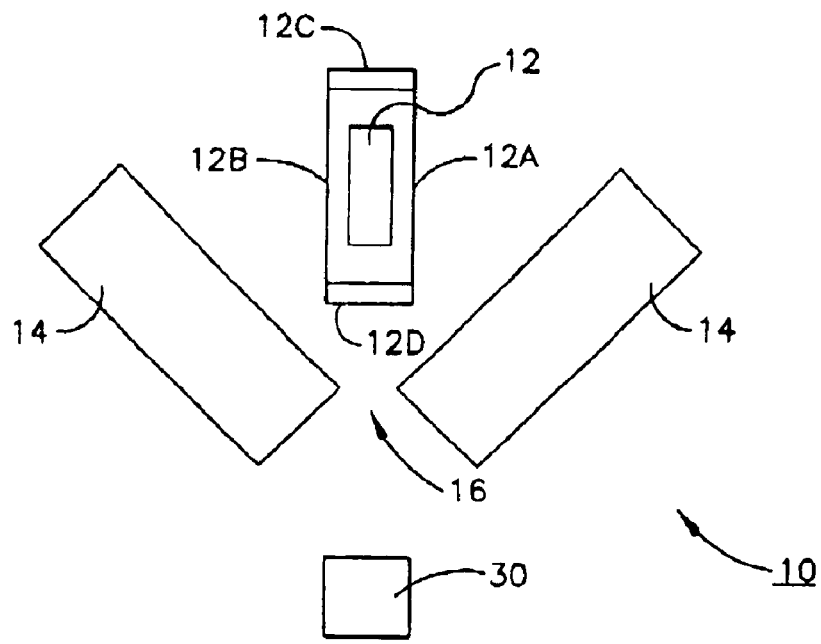
FIG. 1 is a schematic drawing of the apparatus reported in the aforementioned IEEE paper.

Referring now to FIG. 1, that depicts the apparatus reported in the aforementioned IEEE paper, the apparatus 10 depicted in that paper comprised a single position sensitive photomultiplier tube (PSPMT) 12 positioned behind a pinhole collimator shield 14 that provided a single pinhole 16 through which PSPMT 12 viewed seed radiation source 18. Such an apparatus demonstrated the capability of locating radiation seed source 18 in two dimensional space at a depth of up to about 16 cm as reported in the paper.

While such a device and method provided highly useful in vivo tracking or seed source 18 in two dimensions, it clearly provided no indication of the depth at which seed source 18 was located. Thus, seed source 18 could in actuality be located in front of or behind a desired location in the body. Additionally, in those rare instances where seed source 18 became "lost" in the body or a specific body cavity it was difficult to determine the exact location of seed source 18 therein since no depth information was provided by the apparatus and method.

Figure 2:
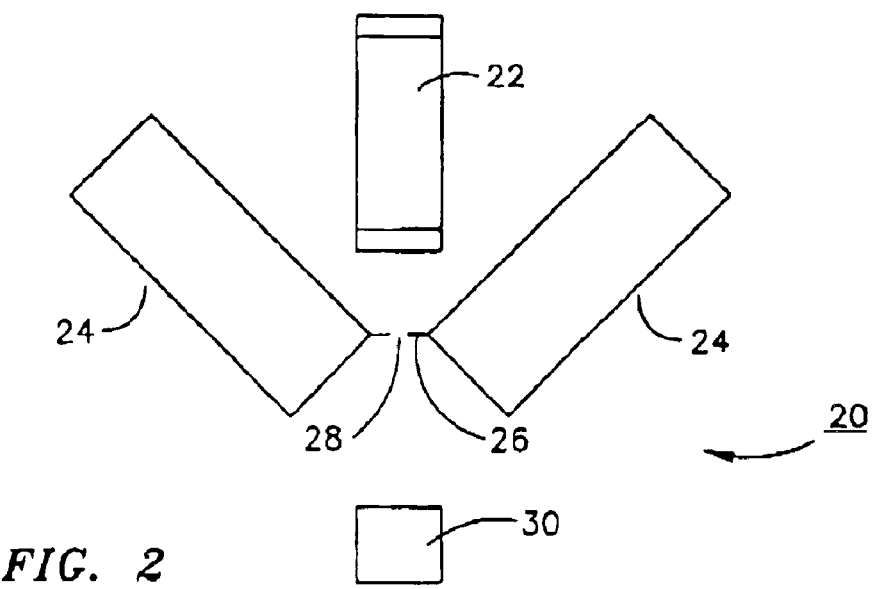
FIG. 2 is schematic drawing of one embodiment of the apparatus of the present invention.

Referring now to FIG. 2 that is a schematic drawing depicting one preferred alternative embodiment of the apparatus of the present invention, the apparatus 20 of the present invention comprises a PSPMT 22 located behind a collimator shield 24 that includes a thin collimator element 26 that includes a plurality (at least two) pinholes 28 therein. In this configuration, PSPMT 22 is capable of acquiring at least two spatially displaced images thereby providing the basis for the reconstruction of a three dimensional image of seed 30. Using state-of-the-art computer software, such images can be integrated to provide the information required to exactly locate seed 30 inside of a body. Thus, the means are provided for obtaining an in vivo image of seed 30 and the information needed to assure the proper location of seed source 30 in a tumor or body cavity during treatment. Similarly, the location information thus obtained could be used to guide a surgeon seeking to retrieve a "lost" seed source within some portion of the body.

Figure 3:
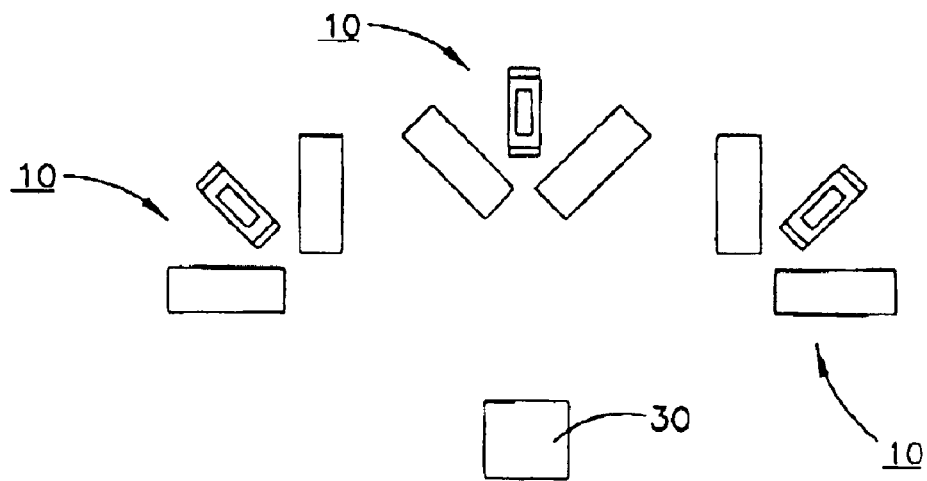
FIG. 3 is a schematic drawing of an alternative embodiment of an apparatus useful in the method of the present invention.

As an alternative to the use of a multiple pin hole arrangement as depicted in FIG. 2, as shown in FIG. 3, a plurality, at least two, single pinhole collimators, as used in the prior art or a plurality of devices, as depicted in FIG. 1, could be used to obtain the required multiple, spatially removed images needed to provide the depth information required to provide the exact, three dimensional location of seed source 30 in the body.

Figure 4:
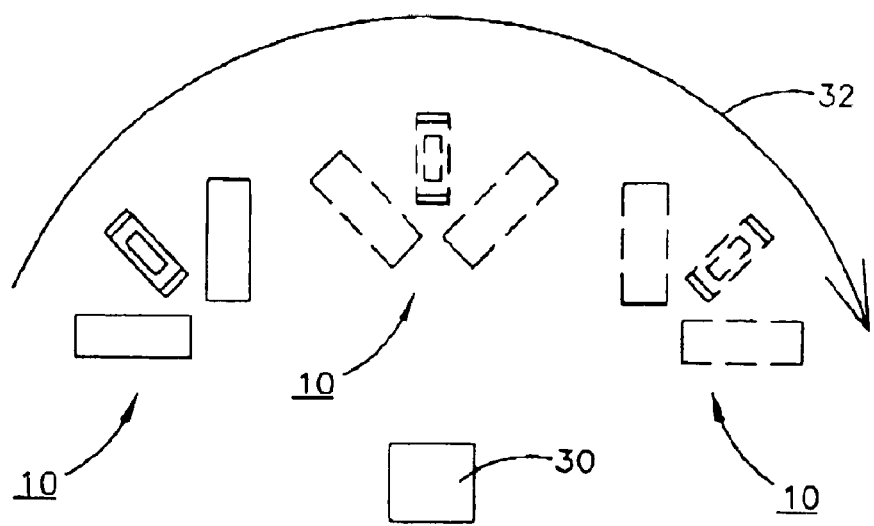
FIG. 4 is a schematic drawing of yet another alternative embodiment of an apparatus useful in the method of the present invention.

As yet a further alternative, one single pinhole device as depicted in FIG. 1, or a multiple pinhole device as depicted in FIG. 2 could be used to make multiple images of seed source 30, as shown in FIG. 4. Such an arrangement also would provide the information required for the reconstruction of a three dimensional image of seed source 30 in the body. In this case a single detector system is moved, for example, along arc 32 to obtain a plurality of images of seed source 30 to provide the required information.

Since the commonly used Ir-192 seed source isotope has many gamma lines spanning mainly the region from 136 to 599 keV. This presents a challenge in providing sufficient stopping power by the collimator material for the high energy components of the emission spectra. It was determined that the best approach to solve this problem was to boost the relative detection efficiency of the lower energy gamma lines emitted by the source by the appropriate selection of the scintillator used, while at the same time lowering the absolute detection efficiency of the detector.

Thus, the small gamma camera is based on a round 5" Hamamatsu R3292 PSPMT, from Hamamatsu, Corporation, Bridgewater, N.J. with the scintillator array described below optically coupled directly to the photomultiplier window. The detector is placed inside of a cylindrical can 12a with a 5 mm thick lead wall on the side 12b and back 12c and an aluminum window 12d 1 mm thick. A conically shaped pinhole mount 14 with 1.5 cm thick lead walls is supported in front of camera 12, Suitable pinhole inserts 16/28 of, for example 0.5 and 1.0 mm diameters are placed on a suitable, for example tungsten, pinhole plug 26. A suitable data acquisition system is a LeCroy PERA ADC system connected via an SCSI to a portable Power PC G3 Macintosh computer running Kmax data acquisition software and image processing software available from Sparrow Corporation, Starkville, Md. Two LeCroy FERA ADC's can be used to provide a total of 32 channels.

While a variety of scintillator materials can be used in the scintillator array that is optically coupled to the PSPMT because of the high intensity of the gamma radiation emitted by the Ir-192 seed source, it is preferable to use a less sensitive scintillator such as a plastic scintillator. Accordingly, according to one preferred embodiment of the present invention a plastic scintillator such as a 0.5 mm thick and 12 cm in diameter Bicron BC-400 available from Hilger crystals Ltd., Margate, Kent, Ukis optically coupled to the photomultiplier window with GE Silicones VISC-60M high viscosity coupling liquid available from General Electric Co., 260 Hudson River Rd., Waterford, N.Y. According to a highly preferred embodiment, the scintillator was further is covered with Millipore GSWP-304 white filter paper to improve scintillation light coupling to the photomultiplier window. It is further highly preferred that the edge of the scintillator disk be coated with a black coating to absorb light internally reflected in the disk. While virtually any suitable scintillator can be used in the successful practice of the present invention so long as adequate steps are taken to adjust for the efficiency of the scintillator, plastic scintillators of the type described above have been found particularly useful due to their relatively low efficiencies and the relatively high gamma emission level of the typically used radioactive seed sources.

In the case where a single detector using a multiple-pinhole or pinhole array mask as depicted in FIG. 2 is used, image reconstruction can be accomplished by back projecting the two dimensional image through each pinhole and using a threshold technique to find the actual source location in three dimensional space.

In the case where multiple camera arrangements are used, the embodiment depicted in FIG. 3, the cameras should be oriented at an angle less than 180°, preferably at an angle of about 90°. Determination of the three dimensional location of the source is achieved by simple backprojection or by maximum likelihood statistical estimation procedures well known in the art. A three dimensional movie or the source location can be generated, either in real-time for the backprojection approach or retrospectively for the maximum likelihood approach, if this cannot be generated in real time. Implementation of the background projection approach is achieved since counts will be high where the backprojected ray paths from high activity pixels intersect, so thresholding the backprojected image so that only the high activity spot remains, perhaps at about 75% of the peak value of the three dimensional region, will yield a three dimensional image of the seed. The threshold value should be greater than the peak background projected pixel value from any single two-dimensional image. If thresholding is not used, then two linear streaks, form the backprojection, and their high amplitude intersection will be seen. Independent of camera position, activity in a reference three dimensional coordinate system can be displayed. Maximum activity projection images onto 3 orthogonal planes can be formed. The value of the projection pixel will be the maximum voxel value in the three dimensional image space along a raypath normal to the image pixel that passes through the source volume. This will allow for easier visualization of the source three-dimensional location.

In the case where a single detector is used in multiple positions (FIG. 4), a mechanism that permits rapid relocation and imaging is required to obtain images in different views that are virtually simultaneous.

There is thus described herein apparatus and a method for tracking the location of a radioactive seed source in the body of a living subject. The method comprises obtaining multiple views of the seed source in the body using: 1) a single detector that is exposed through a multiplicity of pinholes thereby obtaining a plurality of images from a single angle; 2) a single detector that may obtain an image through a single pinhole or a plurality of pinholes from a plurality of angles through movement of the detector; or 3) a plurality of detectors that obtain a plurality of views from different angles simultaneously or virtually simultaneously. The plurality of images obtained from these various techniques through the angular displacement of the various acquired images provide the information required, with the use of imaging software, to generate the three dimensional images needed to define the location of the radioactive seed source in three dimensional space within the body of the living organism.

Thus in practice, one or more of the detectors described herein is aimed at the suspected area of location of the radioactive seed source in the living organism, and the seed source detected and located through the application of the computer based analytical tools described hereinabove to the images obtained from the detectors, to provide a definitive three dimensional image of the location of the seed source within the body.

While the protective screen about the PSPMT as depicted in the various Figures is shown as being cone shaped and described herein as being fabricated from lead, it will be apparent to the skilled artisan, that other screen shapes and materials of fabrication are equally useful. Similarly, while certain computer hardware and image processing software have been described for the successful practice of the instant invention, it will be equally apparent to the skilled artisan that other similarly useful computer hardware and software could be equally well utilized. Additionally, while the film or foil in which the pinhole collimator is located has been specifically described as being fabricated from tungsten, other suitable metals such as aluminum could also be used for this element.

As the invention has been described, it will be apparent to those skilled in the art that the same can be varied in many was without departing from the spirit and scope of the invention. Any and all such modifications are intended to be within the scope of the appended claims.

What is claimed is:

1. A method for tracking a high intensity radioactive seed source in a living organism comprising:
    A) acquiring from outside of the living organism a plurality of images of the high intensity radioactive seed source in the living organism by exposing:
        I) a single position sensitive photomultiplier tube coupled to a low efficiency scintillator viewing the high intensity radioactive seed source in the living organism through a pinhole collimator array;
        II) a single position sensitive photomultiplier tube coupled to a low efficiency scintillator viewing the high intensity radioactive seed source in the living organism through a single pinhole collimator or a pinhole collimator array from a plurality of angles; or
        III) a plurality of position sensitive photomultiplier tubes each coupled to a low efficiency scintillator viewing the radioactive seed source in the living organism through a single pinhole collimator or a pinhole collimator array from a plurality of angles; and
    B) reconstructing the acquired images through computer based analysis and synthesis to produce a three dimensional image of the high intensity radioactive seed source in three dimensional space.

2. The method of claim 1 wherein said position sensitive photomultiplier tube is contained within a protective screen and said pinhole collimator is provided in a plug across an opening in said protective screen.

3. The method of claim 2 wherein said protective screen is cone shaped.

4. The method of claim 2 wherein said plug comprises a film or foil of tungsten.

5. The method of claim 2 wherein said scintillator comprises a plastic scintillator.

6. The method of claim 2 wherein said pinhole collimator is between about 0.5 mm and about 1.0 mm in diameter.

7. The method of claim 2 wherein said images are acquired using a plurality of position sensitive photomultiplier tubes each coupled to a plastic scintillator viewing the high intensity radioactive seed source in the living organism through a single pinhole collimator or a pinhole collimator array from a plurality of angles of less than 180°.

8. The method of claim 7 wherein said plurality of angles are below about 90°.

9. A method for tracking a high intensity radioactive seed source in a living organism comprising:
    A) acquiring from outside of the living organism a plurality of images of the high intensity radioactive seed source in the living organism by exposing:
        I) a single position sensitive photomultiplier tube coupled to a plastic scintillator viewing the high intensity radioactive seed source in the living organism through a pinhole collimator array;
        II) a single position sensitive photomultiplier tube coupled to a plastic _scintillator viewing the high intensity radioactive seed source in the living organism through a single pinhole collimator or a pinhole collimator array from a plurality of angles; or
        III) a plurality of position sensitive photomultiplier tubes each coupled to a plastic _scintillator viewing the high intensity radioactive seed source in the living organism through a single pinhole collimator or a pinhole collimator array from a plurality of angles; and
    B) reconstructing the acquired images through computer based analysis and synthesis to produce a three- dimensional image of the high intensity radioactive seed source in three dimensional space.

10. A method for tracking a high intensity radioactive seed source in a living organism comprising:
    A) acquiring from outside of the living organism a plurality of images of the high intensity radioactive seed source in the living organism by exposing:
        I) a single position sensitive photomultiplier tube coupled to a plastic scintillator viewing the high intensity radioactive seed source in the living organism through a pinhole collimator array;
        II) a single position sensitive photomultiplier tube coupled to a plastic scintillator viewing the high intensity radioactive seed source in the living organism through a single pinhole collimator or a pinhole collimator array from a plurality of angles; or
        III) a plurality of position sensitive photomultiplier tubes each coupled to a plastic scintillator viewing the high intensity radioactive seed source in the living organism through a single pinhole collimator or a pinhole collimator array from a plurality of angles, each of said position sensitive photomultiplier tubes being contained within a protective screen, said pinhole collimators being provide with a plug across an opening in said protective screen and the pinholes in the pinhole collimator are between about 0.5 mm and about 1.0 mm in diameter; and
    B) reconstructing the acquired images through computer based analysis and synthesis to produce a three-dimensional image of the high intensity radioactive seed source in three dimensional space.

11. A method for tracking a high intensity radioactive seed source in a living organism comprising:
    A) acquiring from outside of the living organism a plurality of images of the high intensity radioactive seed source in the living organism by exposing a plurality of position sensitive photomultiplier tubes each coupled to a plastic scintillator viewing the high intensity radioactive seed source in the living organism through a single pinhole collimator or a pinhole collimator array from a plurality of angles less than about 180°, each of said position sensitive photomultiplier tubes being contained within a protective screen, and said pinhole collimators being provided with a plug across an opening in said protective screen; and B) reconstructing the acquired images through computer based analysis and synthesis to produce a three-dimensional image of the high intensity radioactive seed source in three dimensional space.

12. The method of claim 11 wherein said plurality of angles are below about 90°.

* * * * *